United States Patent
Lamont

[11] Patent Number: 5,913,841
[45] Date of Patent: Jun. 22, 1999

[54] MEDICAL BOOT WITH DETACHABLE SOLE FOR WOUND CARE APPLICATION

[76] Inventor: William D. Lamont, 54283 Meadowood Ct., Shelby Township, Mich. 48316

[21] Appl. No.: 08/812,014

[22] Filed: Mar. 6, 1997

Related U.S. Application Data

[63] Continuation-in-part of application No. 08/343,090, Nov. 21, 1994, Pat. No. 5,609,570, and application No. 08/521,962, Aug. 21, 1995, Pat. No. 5,762,622.

[51] Int. Cl.[6] .............................. A61F 13/00; A61F 5/00
[52] U.S. Cl. ................................. 602/65; 602/27; 602/28
[58] Field of Search ................................ 602/26, 23, 60, 602/61, 62, 27; 36/9

[56] References Cited

U.S. PATENT DOCUMENTS

| | | | |
|---|---|---|---|
| 4,832,010 | 5/1989 | Lerman | 602/62 X |
| 5,367,789 | 11/1994 | Lamont | 36/9 |
| 5,569,173 | 10/1996 | Varn | 602/27 |
| 5,569,174 | 10/1996 | Varn | 602/27 |

*Primary Examiner*—Richard J. Apley
*Assistant Examiner*—Kim M. Lee
*Attorney, Agent, or Firm*—Charles W. Chandler

[57] ABSTRACT

A medical boot for protecting a user's foot has a bottom covering formed of a continuous loop material. A detachable, flexible external trilaminate sole has an upper layer of a continuous fabric loop material engageable with the bottom of the boot, a bottom layer of a ground-engaging material, and an intermediate layer of a resilient foam.

7 Claims, 2 Drawing Sheets

MEDICAL BOOT WITH DETACHABLE SOLE FOR WOUND CARE APPLICATION

CROSS-REFERENCE TO RELATED APPLICATIONS

This application is a continuation-in-part of Ser. No. 08/343,090, filed Nov. 21, 1994, now U.S. Pat. No. 5,609,570, for "Protective Medical Boot and Orthotic Splint" and Ser. No. 08/521,962, filed Aug. 21, 1995, now U.S. Pat. No. 5,762,622, for "Medical Boot with Unitary Splint".

BACKGROUND OF THE INVENTION

This invention is related to a medical boot for orthotic or wound care applications having an outer fabric cover formed of a continuous layer of fabric loops that are engageable with fabric hook material, and a trilaminate detachable sole having an upper surface with fabric hooks that are releasably engageable with the fabric loops of the boot sole.

In my prior patents and applications I have disclosed a variety of applications for a soft, flexible fabric boot body that protects a user's heel from decubitus ulcers for patients with heel, toe and foot pressure. I have also disclosed a splint and a hard inner sole that can be mounted in the boot to support the user's foot when he is lying on his back. See for example my U.S. Pat. No. 5,367,789 which was issued Nov. 29, 1994, for "Protective Medical Boot and Orthotic Splint".

In some cases the user may desire to walk while wearing the boot, either with a hard splint, a hard inner sole, or with no stiff structure between the bottom of his foot and the boot sole. For this reason I disclosed a resilient detachable exterior sole in my co-pending application Ser. No. 08/343,090, filed Nov. 21, 1994, for "Protective Medical Boot and Orthotic Splint".

Another form of a resilient detachable exterior sole that could be releasably attached to the medical boot was illustrated in my U.S. patent application Ser. No. 08/521,962 for "Medical Boot with Unitary Splint". The exterior sole has a cushioned mid-section, a bottom laminate with a formed ground-engaging bottom surface, and an upper laminate of a continuous layer of hook-shaped fabric type fastener material which can be readily attached to the bottom cover of the boot. The exterior detachable sole can be readily attached to the boot when the user wants to walk, or be removed from the boot when the patient is lying down.

Some prior art such as U.S. Pat. Nos. 5,569,173 and 5,569,174, which issued to Harold T. Varn on Oct. 29, 1996, for "Foot Orthosis with Detachable Sole Plate" use fabric hook fastener strips that are parallel to the length of the patient's foot. One problem with such strips is that the ground-engaging layer of the detachable sole is relatively thick and stiff. If the strips of fasteners are not sufficiently wide and aligned, the sole separates from the boot as the patient walks. The hole in the sole (Varn) for access to a nut and bolt assembly must register with the hole in the bottom layer of the boot, or misalignment may cause the sole to separate from the boot.

Varn's splint utilizes a nut and bolt to extend a toe piece to create a larger size. This assembly creates a posting area in the mid-section of the foot. Hook and loop strips must be attached on either side of this assembly. The loop strips are sewn to the bottom of the boot to a canvas type fabric, because a laminate type of fabric used in my boot would be too thick and would require a much longer bolt. This would cause unwanted pressure to the plantar surface of the foot. Also, if the nut loosens while the patient is ambulating, the toe piece could shift to the side, and thereby disengage or misalign the sole from the boot. This is especially true for all telescoping splints.

SUMMARY OF THE INVENTION

The broad purpose of the present invention is to provide an improved external detachable sole for a fabric medical boot having a fabric type loop means on the bottom surface of the boot. The preferred detachable sole is about ½" thick with a foam type mid-section, a layer of fabric hook material covering the entire upper surface of the sole and a rubber-type lower layer about 1/16" thick with a formed ground-engaging surface.

Covering the entire upper surface of the detachable sole with fabric hooks increases the total area of attachment between the boot and the sole. Further the foam type midsection obviates the tendency of a fairly flexible fabric boot from separating from a fairly stiff ground-engaging sole layer as the patient is walking.

The detachable sole can be readily mounted in any comfortable position on the bottom of the boot and easily removed when the user has completed walking. The detachable sole can be used either with or without an internal splint or sole of the type disclosed in my U.S. Pat. No. 5,367,789. The sole provides cushioning without adding an undesirable height on the patient's leg.

Still further objects and advantages will become readily apparent to those skilled in the art to which the invention pertains upon reference to the following detailed description.

DESCRIPTION OF THE DRAWINGS

The description refers to the accompanying drawings in which like reference characters refer to like parts throughout the several views and in which.

DESCRIPTION OF THE PREFERRED EMBODIMENT

Figure 1:
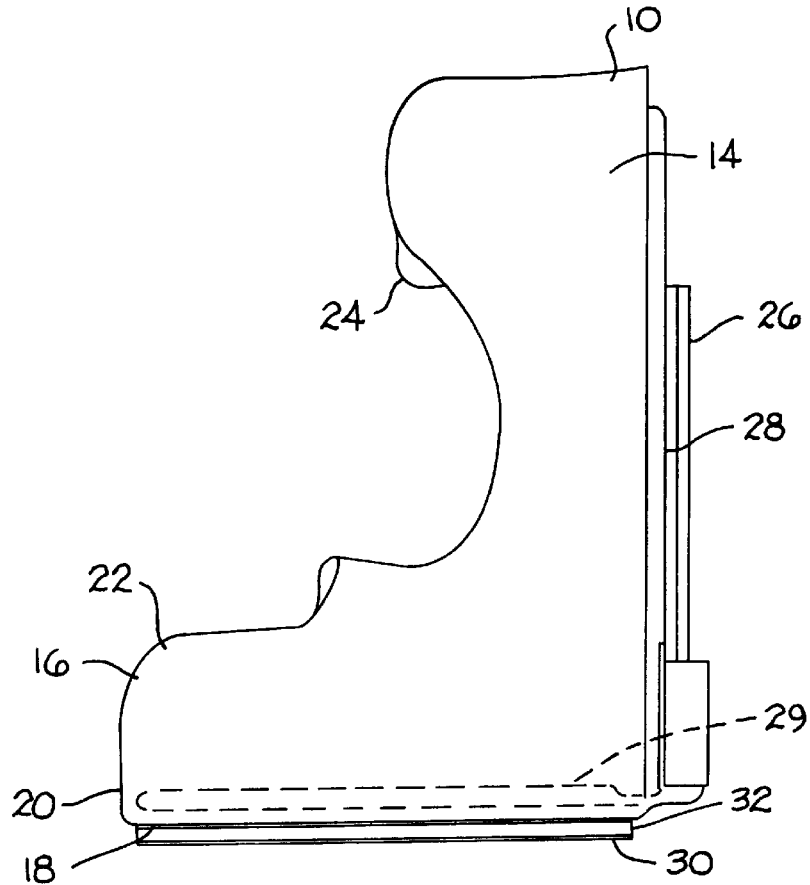
FIG. 1 is an outline of a soft fabric covered orthotic boot with a detachable external sole illustrating the preferred embodiment of the invention.
Figure 2:
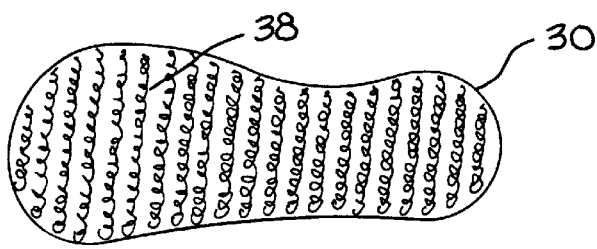
FIG. 2 is a top view of the detachable external sole.
Figure 3:
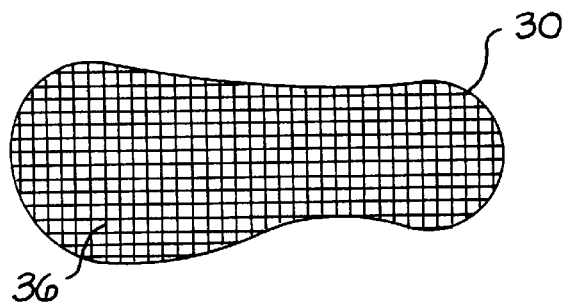
FIG. 3 is a bottom view of the detachable external sole.
Figure 4:
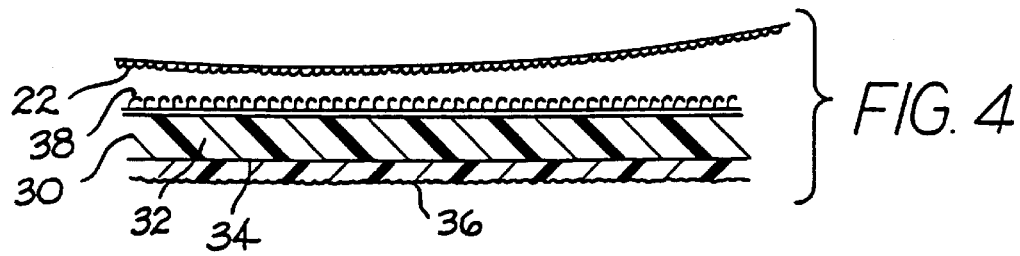
FIG. 4 is an enlarged fragmentary sectional view of a portion of the bottom of the boot sole and the detachable sole.
Figure 5:
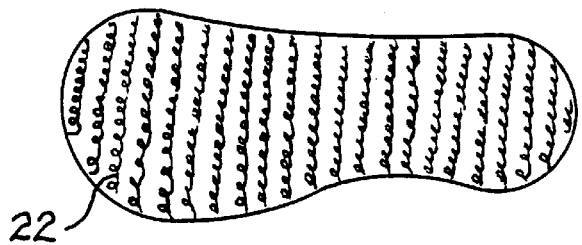
FIG. 5 is an enlarged view of the bottom of the fabric boot sole.

Referring to the drawings, FIG. 1 illustrates a protective medical boot 10 similar to the boot disclosed in my U.S. Pat. No. 5,367,789, issued Nov. 29, 1994, which is incorporated herein by reference. Boot 10 has an upper panel 14 and a foot panel 16 formed with a bottom surface 18. The upper boot panel and the foot panel are each formed of an elastomeric, shape-retaining material such as a soft, flexible, compressible, open core polyurethane foam having an outer cover 20 of a type of cloth characterized by a continuous layer of small fabric loops 22 which makes the material compatible with fabric hook fastener means such as Velcro fasteners. The outer cloth material forming bottom surface 18 is preferably a brushed tricot covering, so that a patch of a Velcro hook material can be releasably connected in any position on the boot.

The upper boot panel has a strap means 24 for encircling the front of the user's leg and connecting the boot to the leg. Other straps may also be employed.

An L-shaped relatively rigid splint means 26 of the type illustrated in my U.S. Pat. No. 5,367,789 may be employed when the patient is in bed. The splint has an external vertical leg 28 and an internal horizontal leg 29.

FIGS. 2–5 illustrates a detachable external sole 30 having squared forward and rear ends is releasable attached to the bottom of the boot to assist the user in walking. Preferably detachable sole 30 is a trilaminate having a thickness of about ½", a length of about 9¼", and a maximum width of about 4". The detachable sole has a cushioned or resilient foam mid-section 32 and a bottom rubber-like laminate 34 about 1/16" thick with a formed ground-engaging knobby bottom surface 36. Surface 36 forms a non-skid surface. The upper side of the detachable sole has a continuous layer of a hook-shaped fabric type fastener material 38 which can be readily releasably attached to the compatible bottom surface 18.

The detachable external sole can be readily attached to the boot when the user wants to walk, or be removed from the boot when the user is lying down. Preferably, the hook-shaped fastener material covers the entire upper surface of the detachable sole to permit the user to have a firm attachment to the bottom of the boot and to permit the detachable sole to be readily positioned in any convenient location on the bottom of the boot.

Figure 6:
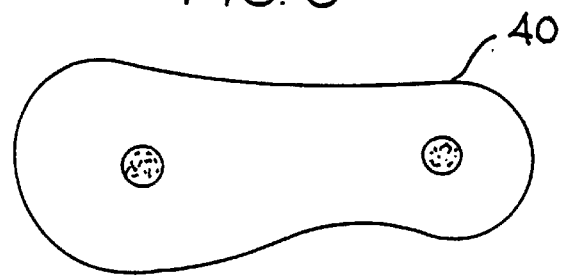
FIG. 6 illustrates a removable inner sole.
Figure 7:
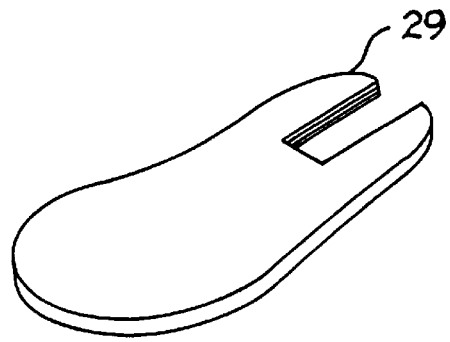
FIG. 7 illustrates a hard inner sole forming part of an L-shaped splint.

The boot may contain a relatively hard inner sole comprising either sole 40 illustrated in FIG. 6 and which is described more fully in my U.S. Pat. No. 5,367,789, and worn inside the fabric boot, or a hard splint leg 29 which forms the horizontal portion of splint 26 also illustrated in my U.S. Pat. No. 5,367,789. Accordingly, the patient can wear the detachable sole with or without the splint, with or without a hard inner sole, or with neither the splint or the hard inner sole.

Figure 8:
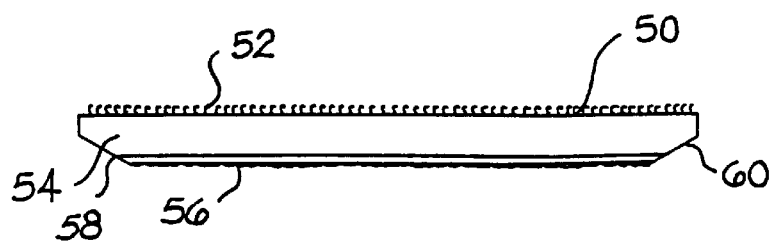
FIG. 8 illustrates a side elevational view of a modified form of a detachable sole.

FIG. 8 illustrates an alternative detachable sole 50 having an upper hook-shaped fastener material 52, a resilient foam mid-section 54, and a bottom non-skid surface 56. The cross section is identical to sole 30, however, sole 50 has its lower surface curved upwardly at its forward end 58 and its rear end 60. This forms what is sometimes referred to as a rocker sole to assist the user in walking with a rocking motion.

Having described my invention, I claim:

1. A medical boot for orthotic or wound care applications comprising:

a flexible boot having a fabric bottom cover and adapted to receive the foot of a patient;

said fabric bottom cover having integral fibrous loop fastener material which extends over the entire bottom surface thereof;

a detachable sole member having a heel, a toe, a width and a sufficient rigidity to support the patient's foot while walking with the flexible boot;

said detachable sole member having a fibrous hook fastener material releasably secured to the fibrous loop fastener material on the bottom surface of fabric bottom cover whereby said detachable sole member can be detached from said boot;

the detachable sole member comprising a trilaminate material including an upper layer of said fibrous hook fastener material, a bottom layer of a rubber-like material having a ground-engaging surface coextensive with said upper layer, and an intermediate layer of compressible resilient foam, wherein the detachable sole member provides a continuous area of compression from said heel to said toe and the full width of the detachable sole for accommodating the weight of a patient's foot disposed in said boot.

2. A medical boot as defined in claim 1, including a second sole member removably disposed in the flexible fabric boot.

3. A medical boot as defined in claim 2, in which the second sole member comprises a portion of an L-shaped splint.

4. A medical boot as defined in claim 2, in which the second sole member comprises a relatively hard sole disposed in the boot generally parallel to the detachable sole member.

5. A medical boot as defined in claim 1, in which the boot includes a lower first fabric panel defining the foot of the boot and an upper second panel defining an upright portion of the boot;

said panels each comprising a resilient foam core, an inner fabric covering, and an outer fabric covering on said core having a loop fastener surface;

said upper panel being adapted to partially surround the wearer's foot and calf including the wearer's toes; and the upper panel having an integral leg strap adapted to span the front surface of the wearer's leg.

6. A medical boot as defined in claim 1, the first releasable interlocking means comprising continuous miniature loops capable of being interlocked with fibrous hook fastener materials, and the second releasable interlocking means comprises fibrous hook fastener material adapted to adhere to mating surfaces of the bottom of the fabric boot.

7. A medical boot as defined in claim 1, in which the detachable sole member has forward and rear ends which are horizontally curved in shape.

* * * * *